United States Patent
Ebel et al.

(10) Patent No.: US 6,592,816 B1
(45) Date of Patent: Jul. 15, 2003

(54) STERILIZATION SYSTEM

(75) Inventors: James A. Ebel, Jacksonville, FL (US); John B. Enns, Jacksonville, FL (US); Peyman Dehkordi, Knoxville, TN (US); Douglas Ingram, Knoxville, TN (US); Allan W. Kimble, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 09/259,796

(22) Filed: Mar. 1, 1999

(51) Int. Cl.$^7$ .............................. A61L 2/10; A61L 2/24

(52) U.S. Cl. ...................... 422/62; 422/22; 250/455.11

(58) Field of Search ................................ 96/1.4; 422/22, 422/24, 186.05, 62; 356/328; 250/455.11

(56) References Cited

U.S. PATENT DOCUMENTS

| | | | |
|---|---|---|---|
| 3,711,746 A | 1/1973 | King ........................ 317/258 |
| 3,817,703 A | 6/1974 | Atwood ........................ 21/2 |
| 3,859,089 A | * 1/1975 | Chambers .................... 96/1.4 |
| 3,907,439 A | 9/1975 | Zanoni ....................... 356/160 |
| 3,941,670 A | 3/1976 | Pratt, Jr. .................... 204/158 |
| 3,955,921 A | 5/1976 | Tensmeyer ................... 21/54 |
| 3,979,696 A | 9/1976 | Buchman ................ 331/94.5 P |
| 4,015,120 A | 3/1977 | Cole ......................... 250/216 |
| 4,042,325 A | 8/1977 | Tensmeyer ................... 21/54 |
| 4,071,334 A | 1/1978 | Kolb et al. ..................... 55/2 |
| 4,077,782 A | 3/1978 | Drummond et al. ......... 55/139 |
| 4,236,900 A | 12/1980 | Fitch et al. ................. 55/138 |
| 4,349,359 A | 9/1982 | Fitch et al. ................. 55/151 |
| 4,464,336 A | 8/1984 | Hiramoto ..................... 422/24 |
| 4,495,313 A | 1/1985 | Larsen |
| 4,518,502 A | 5/1985 | Burns et al. ................. 210/634 |
| 4,524,079 A | 6/1985 | Hofmann .................... 426/234 |
| 4,565,348 A | 1/1986 | Larsen |
| 4,629,896 A | 12/1986 | Bridgen |
| 4,680,336 A | 7/1987 | Larsen et al. |
| 4,695,472 A | 9/1987 | Dunn et al. ................. 426/237 |
| 4,734,917 A | 3/1988 | Johnson ....................... 372/70 |
| 4,766,288 A | 8/1988 | Berkes et al. ............... 219/216 |
| 4,836,859 A | 6/1989 | Konishi et al. ................ 134/1 |
| 4,838,154 A | 6/1989 | Dunn et al. ................... 99/451 |
| 4,867,796 A | 9/1989 | Asmus et al. .................. 131/1 |
| 4,871,559 A | 10/1989 | Dunn et al. ................. 426/248 |
| 4,889,664 A | 12/1989 | Kindt-Larsen et al. |
| 4,910,942 A | 3/1990 | Dunn et al. .................. 53/425 |
| 4,912,720 A | 3/1990 | Springsteen ................. 372/72 |
| 4,989,215 A | 1/1991 | Winik ......................... 372/70 |
| 5,034,235 A | 7/1991 | Dunn et al. ................. 426/238 |
| 5,039,459 A | 8/1991 | Kindt-Larsen et al. |
| 5,048,404 A | 9/1991 | Bushnell et al. .............. 99/451 |
| 5,133,932 A | 7/1992 | Gunn et al. ................... 422/24 |
| 5,196,174 A | 3/1993 | Cerola et al. ................ 422/300 |
| 5,196,458 A | 3/1993 | Nunez et al. |

(List continued on next page.)

FOREIGN PATENT DOCUMENTS

| | | |
|---|---|---|
| DE | 3533825 A1 | 4/1987 |
| DE | 3406421 A1 | 8/1994 |
| EP | 0479723 B1 | * 9/1991 |
| WO | WO 97/43915 | * 11/1997 |

OTHER PUBLICATIONS

Warriner, K. et al., "Inactivation of *Bacillus subtilis* spores on packaging suraces by u.v. excimer laser irradiation", *Journal of Applied Microbiology* 2000, 88, 678–685.

*Primary Examiner*—Elizabeth McKane
(74) *Attorney, Agent, or Firm*—Anne B. Kiernan (57) ABSTRACT

A sterilization system comprising: radiation source; optical and/or electrical sensors; and timing means; wherein the measurement of radiation by the optical sensor is substantially synchronized based on the timing means to the start and end of each pulse of radiation from the radiation source or to the start and end of the exposure of a product to the radiation source.

47 Claims, 4 Drawing Sheets

U.S. PATENT DOCUMENTS

| | | | |
|---|---|---|---|
| 5,232,367 A | 8/1993 | Vassiliadis et al. | 433/224 |
| 5,235,905 A | 8/1993 | Bushnell et al. | 99/451 |
| 5,256,751 A | 10/1993 | Vanderlaan | |
| 5,263,042 A | 11/1993 | Kojima et al. | 372/72 |
| 5,304,584 A | 4/1994 | Nunez et al. | |
| 5,311,223 A | 5/1994 | Vanderlaan | |
| 5,328,517 A | 7/1994 | Cates et al. | 134/7 |
| 5,364,645 A | 11/1994 | Lagunas-Solar et al. | 426/248 |
| 5,390,073 A | 2/1995 | McMillan | 361/327 |
| 5,393,541 A | 2/1995 | Bushnell et al. | 426/237 |
| 5,395,558 A | 3/1995 | Tsai | |
| 5,435,943 A | 7/1995 | Adams et al. | |
| 5,439,642 A * | 8/1995 | Hagmann et al. | 422/22 |
| 5,447,733 A | 9/1995 | Bushnell et al. | 426/237 |
| 5,484,863 A | 1/1996 | Molock et al. | |
| 5,489,442 A | 2/1996 | Dunn et al. | 426/248 |
| 5,500,533 A * | 3/1996 | Ogawa et al. | 250/372 |
| 5,512,123 A | 4/1996 | Cates et al. | 156/272.6 |
| 5,514,391 A | 5/1996 | Bushnell et al. | 426/237 |
| 5,581,573 A | 12/1996 | Tanuma | 372/72 |
| 5,618,492 A | 4/1997 | Auten et al. | 422/22 |
| 5,642,192 A * | 6/1997 | Gordon et al. | 356/328 |
| 5,648,402 A | 7/1997 | Nunez et al. | |
| 5,654,350 A | 8/1997 | Nunez et al. | |
| 5,658,530 A | 8/1997 | Dunn | 422/24 |
| 5,684,058 A | 11/1997 | Nunez et al. | |
| 5,723,096 A | 3/1998 | Bruun-Jensen | 422/301 |
| 5,768,853 A | 6/1998 | Bushnell et al. | 53/167 |
| 5,786,598 A | 7/1998 | Clark et al. | 250/455 |
| 5,801,483 A | 9/1998 | Watanabe et al. | 313/485 |
| 5,851,365 A | 12/1998 | Scobey | |
| 5,900,211 A | 5/1999 | Dunn et al. | 422/24 |
| 6,013,918 A | 1/2000 | Bushnell et al. | 250/454.11 |

\* cited by examiner

STERILIZATION SYSTEM

FIELD OF THE INVENTION

This invention relates broadly to sterilization of medical devices by ultraviolet radiation. More specifically, this invention relates to a sterilization system by which the amount of radiation produced by the sterilization system is measured, and to the method of measuring and controlling the amount of radiation produced by the sterilization system.

DESCRIPTION OF THE RELATED ART

Medical device sterilization processes and in particular commercial contact lens manufacturing sterilization processes typically involve some form of temperature and/or pressure-based sterilization techniques. For example, a hydrophilic contact lens is typically first formed by injecting a monomer mixture into a mold. The monomer mixture is then polymerized (i.e. the lenses are cured). After other optional processing steps, such as quality inspections, the lens is placed in a container with a solution and the container is sealed. The packaged lens is sterilized by placing the container in an autoclave at an elevated humidity, temperature and pressure for an extended period of time, usually at least 15 minutes, and more typically 30 minutes. Although this commercial process produces thoroughly sterilized contact lenses, the batch-wise autoclave sterilization step is time consuming, costly, and inefficient.

European Patent Application No. 0 222 309 A1 discloses a process using ozone, in which packaging material is disinfected in a manufacturing setting. The process involves feeding an oxygen stream into an ozonating chamber, generating ozone from oxygen in the ozonating chamber, placing packaging containers in a sanitizing chamber, feeding the ozone into the sanitizing chamber, and purging the ozone from the sanitizing chamber with sterile air. The process requires that the ozone contact the packaging material for a predetermined time, followed by the sterile air purge step. The process is offered as an alternative to heat-steam sterilization, sterilization by application of electromagnetic radiation, or chemical agent sterilization.

U.S. Pat. No. 5,618,492 discloses a process for producing a sterile contact lens in a sealed container during a continuous production process wherein the contact lens is immersed in an ozone-containing solution within a container during a continuous lens packaging process, and the lens and container are subsequently subjected to ultraviolet radiation primarily to degrade the ozone. This process sterilizes the contact lens and the container.

U.S. Pat. No. 4,464,336 teaches a method of sterilization using a flash discharge ultraviolet lamp, which produces a very large instantaneous output, which is capable of deactivating microorganisms, including *Aspergillus niger*.

U.S. Pat. Nos. 5,034,235 and 4,871,559 disclose the use of intermittent pulses of very intense, very short duration pulses of light in the visible and near visible frequencies to inactivate microorganisms on the surface of food products, and suggest that the method can be used for packages, medical devices, and food products in packages.

U.S Pat. No. 5,786,598 discloses the idea of using a flash lamp system to sterilize contact lenses in a preserved solution in a container, however, there are no conditions defined to accomplish sterility, nor examples which show that sterility can be accomplished.

U.S. Pat. No. 4,629,896 discloses an apparatus for monitoring the intensity of a UV source (for example, a water sterilizer) in which there is an optical detection unit which detects uv radiation and converts that radiation into an electrical signal, so that the intensity of the radiation can be monitored, and when it falls below a certain level the lamp can be shut off.

WO 97/43915 discloses the use of pulsed light to deactivate microorganisms in a contact lens container. Further, it discloses a method of receiving a portion of the pulsed light, generating an output signal in response to the portion of pulsed light received, and determining whether the pulse of light is sufficient to effect a prescribed level of deactivation of microorganisms in the target area. WO 97/43915 discloses that the fluence-per-flash or the spectral content of the flashes can be measured for various regions of the spectrum by using filters. There are long lists of possible pieces of equipment which might be incorporated into the measuring device, but no embodiment or example of such a device is described. WO 97/43915 suggests the use of an ultraviolet calorimeter to measure the energy in a light pulse, and states that it is traceable to international standards; however, an ultraviolet calorimeter only provides a linear response to a specific pulsewidth, specific wavelength and specific intensity of light, and therefore is only traceable to international standards within those specified parameters. Outside of those specified parameters the ultraviolet calorimeter typically has a non-linear response which is not traceable back to the calibration set-up for which there are international standards. Further, it is not appropriate to use an ultraviolet calorimeter to calibrate a photodetector to international standards. An ultraviolet calorimeter only provides a single measurement of the total energy in the ultraviolet range, and does not provide any spectral information. The measurement it provides is an uncalibrated, relative output based upon the pulsed light energy, multiplied by the responsivity of the detector, and multiplied by the bandpass and spatial filtration of the filter which provides the only radiation to the calorimeter. Further, the calorimetric sensor must have a rest period of a minimum of ten seconds between pulses since it is a thermal sensor. If the ultraviolet calorimeter were used to provide instantaneous and in-line monitoring, the process of sterilizing using pulsed light sterilization would be either ineffective or so slow, it would not be desirable.

There still remains a need for a time-efficient, continuous in-line, and cost effective sterilization system comprising a monitoring and control system and method of sterilization for products, particularly medical products, which can be used in the production line and which can measure and control the radiation to assure that every product is sterilized.

SUMMARY OF THE INVENTION

This invention provides a sterilization system comprising: a radiation source, and a monitoring system comprising a sensor; and a timing means; wherein the measurement of energy by said sensor is substantially synchronized based on said timing means to the start and end of a pulse of radiation from said radiation source or to the start and end of the exposure of a product to said radiation.

This invention further provides a method of measuring energy within a sterilization system wherein said sterilization system comprises a radiation source, and a monitoring system comprising a sensor, and a timing means, comprising the step of:

substantially synchronizing based on said timing means the measurement of energy by said sensor to the start and end of a pulse of radiation from said radiation source or to the start and end of the exposure of a product to said radiation.

This invention further provides a method of monitoring energy of a sterilization system wherein said system comprises a radiation source, and a monitoring system comprising a sensor, and a timing means, comprising the step of:

substantially synchronizing based on said timing means the measurement of energy by said sensor to the start and end of a pulse of radiation from said radiation source or to the start and end of the exposure of a product to said radiation.

The sensor is preferably an optical or electrical sensor or both. The optical sensor measures the radiation produced by the radiation source. The electrical sensor measures the voltage and/or current of the radiation source. It is preferred that each sterilization system or monitoring system has at least one sensor, preferably an optical sensor, and more preferred that each sterilization or monitoring system has at least one optical sensor and at least one electrical sensor.

This invention further provides a monitoring system for a radiation source, preferably for sterilization, the monitoring system comprises a sensor and a timing means. In one embodiment, this invention provides a monitoring system comprising one or more optical sensors which comprise an integrating sphere, or cosine receptor, light guide, and a spectroradiometer with or without a timing means for measuring the radiation produced by the radiation source. Alternatively, in another embodiment, this invention provides a monitoring system comprising one or more electrical sensors, which comprise voltage and/or current monitors of the electrical energy of the radiation source for producing radiation.

The sterilization system and method of this invention comprise a radiation source to sterilize products, preferably medical devices. The sterilization system and method can be used to measure the radiation to which the product is exposed. The system and method described herein are well-suited for in-line manufacturing, and will provide accurate measurements of the radiation to which a product is exposed to assure that every product receives a sterilizing dose of radiation.

The sterilization system and method, when the sensor is an optical sensor, can further be used to measure the radiation at multiple locations in the treatment area of the radiation source and provide a detailed two or three dimensional mapping of the radiation to produce a spatial distribution characterization map of the source itself. In this modality the sterilization system is used as an automated source mapping system. The maps can be used to ensure consistency from one radiation source to another to maintain uniformity in the sterilization dose in the manufacturing process.

DESCRIPTION OF THE INVENTION

The term "sterile" or "sterilization" as used herein means rendering an organism incapable of reproduction.

The term "radiation source" can mean one or more radiation sources unless otherwise indicated.

The term "ultraviolet radiation" means radiation having a wavelength or wavelengths between 200 nm and 400 nm.

The sterilization system is preferably used to sterilize medical products, preferably contact lenses in sealed containers or packages. The sterilization system comprises a radiation source, which can be any type of radiation source, including continuous and pulsed radiation sources. The preferred radiation source is a pulsed radiation source, for example, a flash lamp, which is a radiation source that has high intensity for a short time. The preferred pulsed light system is made by PurePulse Technologies, and is further described in WO 97-43915, U.S. Pat. Nos. 5,034,235, 5,786,598, and 5,768,853, and 4,871,559, and 4,464,336 (Hiramoto), all incorporated herein by reference. The preferred radiation source in the sterilization system is further described in concurrently filed Brown-Skrobot, et al, U.S. patent application Ser. No. 09/259,758, entitled "Method of Sterilization", VTN-388, which is incorporated herein by reference. Presently, it is preferred that the pulsing, also referred to as flashing, delivers more than 18 mJ/cm$^2$ ultraviolet radiation having wavelengths between 240–280 nm energy per pulse, preferably more than 30 mJ/cm$^2$ ultraviolet radiation having wavelengths between 240–280 nm per pulse, to all the surfaces of the medical device to be sterilized. The preferred medical device is a contact lens, which preferably is in a sealed container or package. The description which follows will refer to contact lens packages; however, medical devices, other goods or products which may or may not be within containers or packages can be substituted for the contact lens package in the description.

The radiation per pulse may be from one or more radiation or light sources. (The terms light and radiation will be used interchangeably herein.) If the radiation is from more than one source, it is preferred that the sources pulse at the same time or at substantially the same time, that is, within 25 microseconds, more preferably within 5 microseconds and most preferably within 1 microsecond.

The sterilization system further comprises a monitoring system. The monitoring system preferably comprises a sensor. The sensor can be one or more optical or electrical sensors or both. The preferred embodiment comprises at least one optical sensor, more preferably two optical sensors.

The optical sensor preferably comprises a means for collecting the radiation, and means for measuring the radiation. The means for collecting can be a light guide, such as a liquid-filled light guide or a fiber optic, catadioptric mirror, light pipe, input slit, ultraviolet lens, integrating sphere, cosine receptor or multiples or combinations of the preceding list. An integrating sphere and cosine receptor are the more preferred. An integrating sphere is the most preferred.

Integrating spheres typically offer the largest field of view for collecting the radiation and are very durable. In comparison, a quartz fiber optic is less preferred, because it tends to undergo solarization; that is, lose its ability to transmit over time if it is directly exposed to the radiation. An integrating sphere, which comprises numerous durable reflective surfaces, collects at least a portion of the radiation, attenuates or magnifies the intensity of the radiation, and then sends the radiation via a light guide, preferably a fiber optic, to the means for measuring the radiation. Alternatively, the means for measuring the radiation may be incorporated into the means for collecting the radiation or visa-versa, but to limit the size of the means for collecting the radiation which preferably is located near the radiation source, it is presently preferred to have a separate means for measuring the radiation and locate the means for measuring the radiation away from the radiation source.

It is important to limit the size of the means for collecting the radiation, because any object near the radiation source may block some of the radiation which would otherwise reach the product which is very undesirable. The means for collecting the radiation may transfer the collected radiation to the means for measuring the radiation by mirrors, fiber optic, light pipe, ultraviolet lens, or the like; however, it is preferred to use a fiber optic, because it offers flexibility in positioning as compared to methods which would require fixed alignment between the means of collecting the radiation and the means for measuring the radiation.

The integrating sphere is a hollow sphere, typically coated internally with a white diffusing material having a defined spectral reflectivity in the interior of the sphere. The integrating sphere has at least one entry port. It is preferred that the integrating sphere has two or more entry ports. The number of entry ports preferably matches the number of light sources; therefore, for the presently preferred sterilization system it is most preferred that the integrating sphere has two entry ports. The integrating sphere may be located anywhere as long as it receives at least a portion of the light; however, the integrating sphere is preferably located parallel to the package to be exposed, between the light sources, but not blocking any direct light to the packages. In this preferred location, the entry ports are preferably located on the integrating sphere at from 30° to 60°, more preferably from 40° to 50°, and most preferably 45° from the midpoint of the package to be exposed. In these preferred locations, the solid angle for the light cone entering each port will overlap the radiation source. The geometry of the entry port or ports is used to determine the energy per area of the radiation delivered to the packages.

Light traps, exit ports or gray reflector ports in the integrating sphere may be used to attenuate or multiply the radiation to meet the needs of the means for measuring the radiation. Preferably, the integrating sphere will transmit to the means for measuring the radiation enough energy to be near the radiation saturation level for the means for measuring the radiation during each pulse in order to increase the signal to noise ratio. The reflectivity of the integrating sphere material is characterized in order to accurately calculate the sphere multiplier and maintain NIST traceability. Also, the reflectivity of the integrating sphere preferably is as flat as possible across the entire spectral region of the radiation to be measured so that it is matched to the response of the means for measuring the radiation for appropriate gain control across the entire region. Stated differently, the integrating sphere preferably transfers a substantially equal percentage of the radiation at all the wavelengths to be measured by the means for measuring the radiation. Integrating spheres provide to the means for measuring the radiation a much more equal percentage of the light over a range of wavelengths than would be provided, for example, by filters. The preferred integrating sphere collects radiation at all the wavelengths generated by the radiation source.

The means for measuring the radiation preferably can measure total radiation, and the radiation at particular wavelengths or ranges of wavelengths. The means for measuring the radiation is preferably a spectrometer. It is preferred that the input into the spectrometer is a spread fiber optic input. The spectrometer preferably comprises a dispersive optical element and a photodetector. The dispersive optical element can be transmissive or reflective as long as it disperses the radiation into the spectral components of the radiation. Examples of dispersive optical elements which can be used in the spectrometer include diffraction gratings (blazed echelle, holographic, ion-etched), diffractive optics (lenses, windows, mirrors), binary optics (lenses, windows, mirrors), filters and mirrors (holographic, dichroic, narrowband, cut-on, cut-off, thin film, ultraviolet, dielectric, blazed, diamond grooved), lenses and windows and prisms, and rulings, (glass, plastic, lithographic, microlithographic, radial, replicated), optical fibers (glass, liquid, dispersion shifted, plastic) as long as the optical element disperses the radiation into monochromatic radiation or into spectral components, preferably into spectral components. The preferred dispersive optical element is a diffraction grating reflector. The preferred diffraction grating reflector is a holographic grating or a ruled grating. The more preferred spectrometer comprises both a spread fiber optic input and a diffraction grating reflector. The dispersive optical element is preferably focused onto the photodetector.

The photodetector can be any kind as long as it can count the numbers of photons present at a certain range of the wavelength or wavelengths, for example, it can consist of photomultiplier tubes, photodiodes, and photocells in a Charge Coupled Device (CCD) array. The preferred photodetector is a photodetector array, more preferably a photodiode array, most preferably a metal oxide semiconductor (MOS) linear sensor, like the Hamamatsu S3901-256Q photodiode array in the Zeiss MMS miniature spectrometer. There can be any number of photodiodes, for example, at least 32 diodes, preferably there are 128 or more photodiodes, and more preferably 256 or more photodiodes in the array. In the most preferred spectrometer there are 256 photodiodes in an array on a single chip. The grating disperses the radiation into its spectral components which impinge on the array of photodetectors which count the numbers of photons present in the light at the wavelengths for which the photodectors are positioned. The sensor preferably has a spectral response extending down into the UV-C region, e.g. 200 nm, of at least 20 mA/W radiant sensitivity. The spacing of the photodetector array sensors preferably is 60 microns or less, more preferably between 20 and 60 microns. The sensor spacing preferably is calibrated for the x-axis (wavelength) using a second order polynomial fit equation. Preferably, the wavelength resolution of the photodetectors in the spectroradiometer is less than 10 nm, preferably less than 3 nm and is more preferably less than 1 nm. The preferred spectroradiometer, as described, can produce a spectral irradiance chart as a function of wavelength.

The means for measuring the radiation can be a single or small number of photodetectors, that is, less than 32, or less than 10 or even less than 3 photodetectors, which are sensitive to a narrow wavelength range of radiation. The photodetectors can be such that they are sensitive to particular wavelengths of radiation. This would be particularly suited for a radiation source, which produces a limited range of wavelengths, for example, lasers.

The preferred spectrometers are sensitive to the wavelengths between 185 nm and 900 nm. However, spectrometers having a larger or smaller array of photodetectors which are sensitive to a larger or smaller total range and/or larger or smaller incremental ranges of wavelengths within the total range of wavelengths can be used. The spectrometers are selected to have sensitivities to the wavelengths that need to be monitored. Presently, it is preferred that, at a minimum, the spectrometers are sensitive to wavelengths from 200 to 400 nm, more preferably from 200 to 300 nm and most preferably from 240 to 280 nm, because radiation of those wavelengths has the biggest impact on microorganisms.

Preferably both the wavelength and irradiance sensitivity of the spectrometer is calibrated using a NIST source for each; one source having a known irradiance radiation intensity output, and one source having a known spectral signature output. After the spectrometer is calibrated for both its spectral sensitivity and irradiance response with the NIST sources, it becomes a spectroradiometer. The gain or attenuation factor of the integrating sphere, if used, is taken into consideration during calibration. The calibration changes the raw data from the spectrometer, which is in counts per pixel, into calibrated readings of irradiance per wavelength in units of $(mJ/cm^2)/nm$, also referred to as spectroradiometric flux. Preferably, circuitry is added to the spectrometer including an analog to digital converter along with the associated software drivers which allow it to communicate with a computer, for storing the measurements or using the measurements to control the sterilization system.

The monitoring system of the sterilization system further comprises a timing means. The timing means provides that the optical sensor substantially only measures the radiation from the radiation source during each pulse of radiation or only for the time a package is exposed to the radiation source for a continuous radiation source. For either of these embodiments it is preferred that the radiation is collected and measured for substantially 100% of the time that the package is exposed to radiation. For a pulsed radiation source, each individual pulse of radiation is collected and measured individually. It is preferred to synchronize the collection and/or measurement of the radiation with the delivery of radiation to a package, particularly for a non-continuous radiation system, and otherwise deactivate the optical sensor between pulses to prevent the dark current from saturating the sensor, and causing erroneous radiation measurements. If a package is to receive multiple pulses to achieve sterilization, the radiation is collected and/or measured only for the time the radiation source delivers radiation to the package and not during the time between pulses, and the total amount of radiation delivered to the package is determined by summing the measured radiation at particular wavelengths or all wavelengths for each package exposed. For example, in the preferred embodiment, the pulse of radiation lasts approximately 500 microseconds, so the spectrometer is activated for 600 microseconds beginning approximately 20–50 microseconds before the pulse and ending 50–80 microseconds after the pulse. The 20–80 microseconds are buffers to be sure the total radiation during the pulse is collected and measured. The total buffer for each pulse should preferably be more than 50 microseconds and less than 100 milliseconds. Optionally and preferably, the dark current radiation is dumped from the optical sensor within 100 milliseconds before measuring the radiation from the source. Further, it is also preferred that the background radiation is collected and measured shortly prior to the delivery and measurement of any of the radiation from the source, and that the background radiation is subtracted from the total radiation measured from the source. The background radiation is preferably determined by activating the optical sensor for the same duration of a pulse or delivery of continuous radiation to a package, but when no radiation is produced by the radiation source. After the total radiation from the source is measured, the background radiation can be subtracted from the total radiation, and the net radiation can be compared to a standard amount or range of radiation needed for sterilization.

The timing means controls when the optical sensor collects and/or measures the radiation. The timing means can be mechanical or electronic or a combination of both. The timing means can be a timer or clock which is used to activate the optical sensor by the occurrence of some event, such as: an instruction to fire a radiation source, a response from the radiation source that it will fire, or the movement of a package into the chamber to receive a sterilizing dose of radiation, as long as the event will provide enough time for the optical sensor in response to the event to be ready to measure the entire dose of the radiation to the product plus any buffer time allowed, that is, an event prior to the delivery of radiation by the radiation source. The timing means is not the detection of the radiation from the radiation source that is used to sterilize the package, because then the necessary response time of the optical sensor will result in the measurement of less than all of the sterilizing radiation directed at the package. The timing means can be a mechanical, electrical or optical switch or lever which can be activated before, during or preferably after the movement of a package into the housing to receive a sterilizing dose of radiation, and which can optionally be deactivated before, during, or after the movement of the package out of the housing. The movement of the package may activate a switch or lever which would simultaneously cause the radiation source to discharge and the optical sensor to measure, and the switch would be deactivated when the package is removed which would deactivate both the radiation source and the optical sensor. Alternatively, if the radiation source is continuous, the switch just described would only activate and deactivate the optical sensor when the package is placed into and removed from the target area where it is exposed to the radiation from the radiation source. Alternatively, the switch or lever, preferably an electronic gate, may activate individual timers for the radiation source and/or the optical sensor so that the optical sensor will be activated to measure the radiation for a known time that the radiation source will discharge, plus any buffers. The preferred timer is a solid-state electronic timer.

The preferred sterilization system further comprises a computer. In the preferred embodiment, the timing means is incorporated into the synchronization interface which is interfaced to the computer. The timing means and the computer preferably control both the optical sensor, and the radiation source so that the optical sensor is turned on and measures the radiation for the duration of the radiation source, and then the optical sensor is deactivated. The duration of a pulse of radiation is known and a timer causes the optical sensor to activate and deactivate based on the pulse timing for a known duration. In the preferred sterilization system, the computer initiates the radiation source firing sequence while synchronously operating the optical sensor. When the computer sends the radiation source fire, e.g. LAMP FIRE command, a signal is generated electronically to activate the radiation source, and the computer awaits the LAMP-FIRING response. When the radiation source receives the command signal, it activates an internal firing sequence and initiates firing, and also signals that the radiation source will fire via a LAMP-FIRING electronic signal. When the synchronization circuitry in the synchronization interface computer recognizes the LAMP-FIRING signal, it begins a timer. The radiation source requires a known amount of time, or delay, to prepare for a pulse. The timer indicates to the synchronization circuit when to generate a signal to the spectrometer, which will activate the spectrometer at the start of the radiation source and the timer will also send a signal to inactivate the spectrometer at the end of the pulse. Due to the requirement for a fast real-time response, this function is preferably implemented in hardware instead of software. The synchronization circuit is preferably optically isolated from the circuitry for the radiation source, and preferably shielded from any electromagnetic interference or noise from the radiation source. This means that the signal wires from the radiation source to the synchronization interface are preferably not connected directly, but pass information via an optical isolation board, which typically terminates the electrical signal on each side of a solid state optical signal generating transmitter/receiver pair, across which no electrical spike can traverse, to avoid permanent and costly damage to one or both systems.

In the present embodiment, the pulse does not occur instantly, so there is time between the LAMP-FIRING signal and the actual radiation source. During this dark period, preferably one or more steps occur to ensure the measurements by the spectrometer are as accurate as possible. The first step removes (dumps) all the charges on the photodetector prior to opening the shutter to the spectrometer. By timing the dumping of dark current in the photodiodes to within as few milliseconds as possible of the actual flash event, preferably less than 200 milliseconds, more preferably less than 10 milliseconds, minimal error builds up in the radiation measurements from accumulation of dark current. The second step measures the background radiation for the same time interval as the duration of the flash to collect and measure the background radiation. This measured amount can then be subtracted from the measured amount of radiation to correct for the background radiation collected during a radiation source. This step can be performed once, for each of a set of pulses delivered to one or more packages, preferably for each package, and the amount of background radiation is preferably subtracted from each of the measured pulses.

In the preferred embodiment, the system can optionally have one or more, preferably two diagnostic photodiodes to monitor the output of the top and bottom lamps. These photodiodes (which are separate from the photodiodes in the spectrometer) can monitor the pulse timings via a fiber optic connection into the housing which will tell the computer if the radiation source is firing and/or not firing when expected by the optical sensor. These photodiodes preferably also read the residual radiation from the radiation source (if any). This feature detects a defective radiation source or erroneous pulse. Preferably this feature will detect any erroneous pulses during the dark time periods not measured by the spectrometer, or timing discrepancies in the pulsed radiation between what the spectrometer expects and what the sterilization system provides.

In the preferred sterilization system, the spectrometer is synchronized to each pulse, and can measure the spectroradiometric flux for a pulse frequency of up to 1000 pulses per second, preferably 1 to 100 pulses per second, most preferably 3 to 10 pulses per second depending on the pulse width and required dose per package for sterilization. Presently, multiple pulses are required to sterilize the contact lens package. The preferred optical sensor requires very little time to recover from one measurement of radiation to be ready to measure the next pulse of radiation. The optical sensor can measure the spectroradiometric flux of individual pulses of radiation, which are delivered with less than 5 seconds, more preferably less than 1 second, and most preferably less than 300 milliseconds between the pulses. The sterilization system described herein is capable of measuring the total and/or spectral content of the radiation from each individual pulse, and the cumulative radiation of multiple pulses measured for each individual pulse and then summed.

After the optical sensor collects and measures the amount of energy for the specified wavelength or wavelengths or spectrum of wavelengths, this amount or amounts are compared to specified amounts stored in the computer that are needed for the application, which for the preferred embodiment is an amount needed to provide a sterilized product. If the amount of radiation produced by the radiation source, either as individual flashes or cumulatively over multiple flashes, is too small for the application, the system will provide some indication to an operator or online manufacturing controller, or automatically repeat the radiation treatment, or reject the product that was not properly sterilized. A record of each radiation treatment can be stored in the computer so that if the amount of radiation continues to fall short of the standard, then the computer can be programmed to automatically shut-down the sterilization system until it is repaired. Additionally, the amount of radiation can be compared to a maximum amount of radiation above which the polymer of the product or packaging is degraded, resulting in rejection of the product if the maximum is surpassed. The monitored ranges of radiation will preferably be both for the total radiation to which the product is exposed and also for the total amount of radiation of certain wavelengths or ranges of wavelengths that are most destructive to microorganisms. Further, the system can be designed to preferably detect any stray or extra flashes, and to automatically shutdown the sterilization system until the radiation source is repaired. The preferred use of this sterilization system will be in a manufacturing line; therefore, this system may be tied into a larger process control system for the manufacturing line which will either divert product from a malfunctioning radiation source, or shut-down a manufacturing line if necessary.

The radiation measured by the optical sensor is preferably correlated to a spatial distribution of the radiation in the volume where the packages are present in the housing which is prepared for the radiation source prior to using it for sterilization. This correlation, an external correlation, is determined by mapping, that is, by measuring the radiation at multiple points in the volume to be occupied by packages and the optical sensor in the housing so that the entire output field, also known as a map, may be known to within the limits of normal variation. The distribution is determined by moving the optical sensor to one or more, preferably to many, locations within the housing in the radiation field of the radiation sources and measuring the radiation at each location or by using multiple optical sensors at various locations within the radiation field. The radiation measured at the various locations in one, two or three dimensions, is stored in a computer, and the spatial distribution is generated from the stored data preferably by using data fusion techniques. Once this spatial distribution for a radiation source has been established, if the energy is known at one location, i.e. where the means for collecting the radiation is located, then the energy impinging on the product can be determined by using the spatial distribution.

A second correlation, an internal correlation, is particularly useful when the product to be sterilized by this invention is in a package. The internal correlation may be mapped by measurement or calculation based on optical transmissivity of the package material and/or its contents to determine the energy within the package. The optical transmissivity can be determined by using the sterilization system by inserting the means for collecting the radiation inside the package to be sterilized. Either the internal correlation or external correlation or both correlations can be used to determine the amount of radiation necessary for sterilization of the product.

Another embodiment of the invention is the use of more than one optical sensor. Each sensor is given a number N, so that there are N data sets taken at various points within the exposure volume. Using data fusion techniques, the sensor array data points are correlated to produce the 3D map at the surface of the medical device. This data map combines spatial, spectral, and irradiance information, as well as an optional temporal mapping. Comparing maps taken at different times gives an idea of what type of deterioration or aging of the radiation source and/or reflectors is occurring.

The sensor in the sterilization system or the monitoring system for the sterilization system of this invention can be an electrical sensor, instead of an optical sensor. In the preferred embodiment, there is both an optical sensor and an electrical sensor in the sterilization system or monitoring system of this invention. The electrical sensor preferably measures the voltage or current of the electrical energy in the radiation source during either a pulse of radiation from the radiation source or from the start to the end of the exposure of a product to the radiation from the radiation source. The electrical sensor preferably measures both the voltage and the current, or two electrical sensors are used, one of which measures the voltage, and the second of which measures the current. The electrical sensor preferably is a time dependent collection device, meaning that it can measure the change in the voltage and/or the change in the current over the time of the pulse or exposure of the product to the radiation. Preferably the electrical sensor has circuits which digitize the measured levels of voltage and/or current for communication to a computer which compares the levels of voltage and/or current to standard ranges which are required for the radiation source to produce a sterilized product. If the voltage and/or the current to the radiation source, is insufficient or too much either in an individual flash or over multiple flashes, the system will provide some indication to an operator or online manufacturing controller, or automatically repeat the radiation treatment, or reject the product that was not properly sterilized. A record of the voltage and/or the current for each radiation treatment can be stored in the computer so that if the amount of voltage and/or the current continues to fall short of the standard, then the computer can be programmed to automatically shut-down the sterilization system until it is repaired. Further, the electrical sensor can be designed to detect any stray voltage or current, and if detected, to automatically shutdown the sterilization system until the radiation source is repaired. Preferably the timing means, the synchronization interface, the radiation source, and the computer interacts with the electrical sensor as described above for the optical sensor. It is preferred to have an electrical sensor and an optical sensor in the sterilization system, because if there is a problem with the radiation source, it can be diagnosed using the measurements from the electrical and optical sensors. The measurements from the optical and electrical sensors can also be used for troubleshooting and preventive maintenance.

Figure 1:
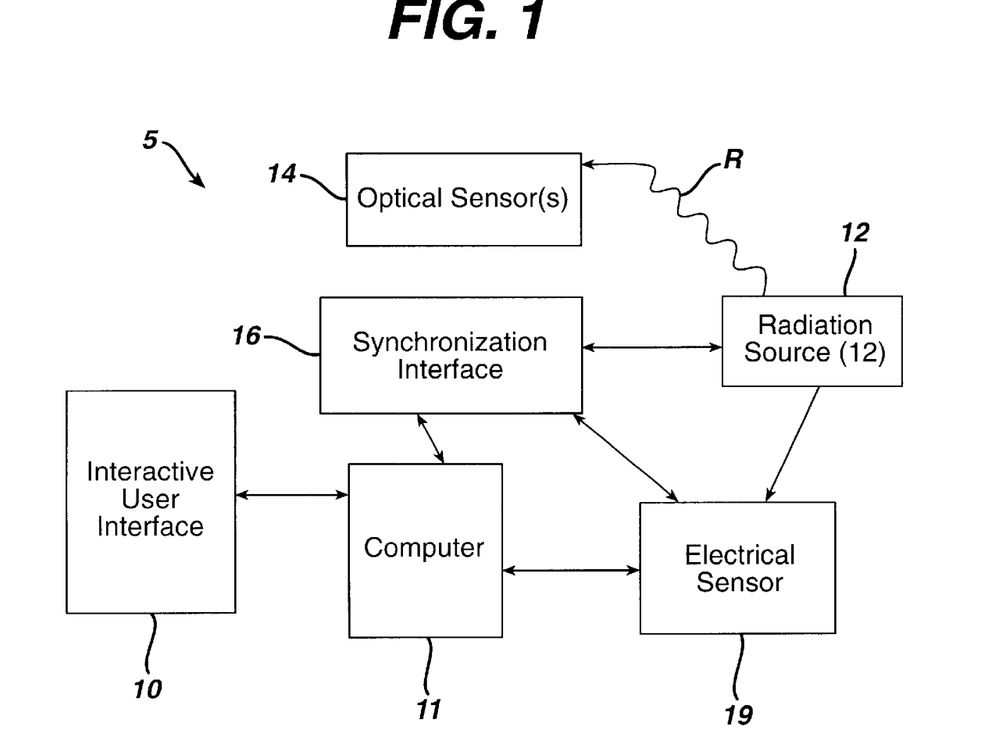
FIG. 1 is a functional block diagram of a sterilization system of this invention.

The preferred block diagram of the invention is shown in FIG. 1. The preferred sterilization system 5 comprises an optional interactive user interface 10, a computer 11 the radiation source 12, the optical sensor(s) 14, an electrical sensor 19, and the synchronization interface 16. The synchronization interface 16 comprises the timing means which comprises a hardware synchronization algorithm using field programmable gate array technology. The synchronization interface 16 interfaces with the radiation source 12, the electrical sensor 19, the optical sensor 14, and the computer 11. The computer 11 comprises control, data fusion, measurement, and logic algorithms, as well as mass storage. Preferably, the computer has one or more algorithms to control separately or in combination the duration, intensity, frequency and number of radiation pulses. An operator can start the sterilization system by controls in the interactive user interface 10. The interactive user interface can be used to turn the sterilization system 5 on and off, adjust the number of flashes per product and set the time between flashes. If the radiation source 12 has additional variables which can be controlled, such as energy levels, wavelength selection, distance between the radiation source and the package, etc., the interactive user interface 10 can be designed to allow the operator to input these controls for the radiation source 12. This information is preferably sent from the interactive user interface 10 to the computer 11 which uses the operator inputs according to its programming to instruct the synchronization interface 16, optical sensor 14, and the radiation source 12 to synchronize their operations so that the radiation shown by arrow R is measured by the optical sensor 14 and the electrical pulse of the radiation source is measured by the electrical sensor 19 only while radiation R is produced by the radiation source 12. After the radiation source 12 produces radiation and the optical sensor 14 has measured the radiation, and if necessary converts analog information into digital information, the optical sensor 14 sends this information to the computer 11 which compares the measured quantity of radiation with a standard, and if the standard is not met, the computer 11 is programmed to communicate the unsatisfactory level of radiation to the radiation source via the synchronization interface 16 to stop the radiation source 12 from producing radiation, to communicate to the interactive user interface 10 that the radiation level was not within the standard, and/or to sound an alarm. Also, after the radiation source 12 produces radiation and the electrical sensor 19 has measured the voltage and/or current in the radiation source 12, and if necessary converts analog information into digital information, the electrical sensor 19 sends this information to the computer 11 which compares the measured quantity of voltage and/or current with a standard, and if the standard is not met, the computer 11 is programmed to communicate the unsatisfactory level of voltage and/or current to the radiation source via the synchronization interface 16 to stop the radiation source 12 from producing radiation, to communicate to the interactive user interface 10 that the voltage and/or current was not within the standard, and/or to sound an alarm. For either of the prior occurrences, computer 10 will store the measurements in a device history file and preferably label it as an unsatisfactory exposure sequence. If the measured radiation and voltage and/or current meet the standards, then the system is programmed to continue its operation, or wait for the operator to send additional instructions. The computer 11 is preferably designed to store all the measured radiation and voltage and/or current per flash for each package which is gathered from the electrical sensor 19 and optical sensor(s) 14.

If this system is integrated into a manufacturing line, the computer can be further programmed to automatically adjust the above-listed variables, such as energy to the radiation source or distance to the product, if insufficient or too much radiation reaches the package. For example, if the amount of ultraviolet radiation as a fraction of the total radiation is too small, then the computer can direct the radiation source interface to increase the voltage of the radiation source which, in the present embodiment, will both produce more total radiation and increase the portion of ultraviolet radiation in the total radiation produced. Further, if this system is integrated into a manufacturing line, the computer can be further programmed to communicate with other various automation controllers such as but not limited to, for example, PLCs, indexers, servo controllers, stepper motor controllers, and other such devices which can be utilized to modify the radiation source in such a way as to generate the appropriate amount of ultraviolet radiation.

Figure 2:
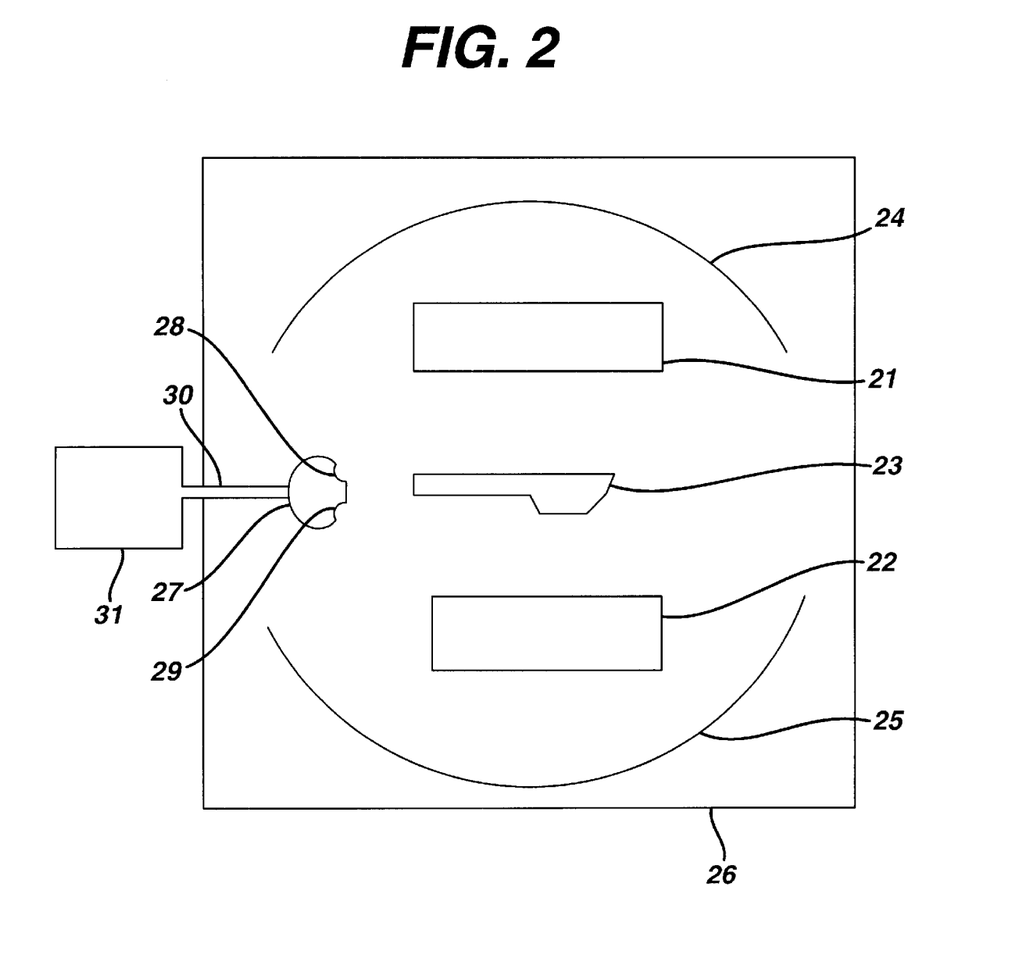
FIG. 2 shows an embodiment of the sterilization system of this invention.

The preferred embodiment of the sterilization system having a contact lens package within the system shown in FIG. 2. It is preferred that the two radiation sources 21 and 22 face each other and that at least one contact lens package 23 which is to be sterilized is placed between the radiation sources, preferably on a quartz plate, not shown. It is further preferred that the radiation sources have reflectors 24 and 25 which reflect the light toward the package(s) 23, and that the reflectors, radiation sources and packages are completely enclosed in a light-tight housing 26 while the radiation sources pulse, so that, when the system is shown in FIG. 2. It is preferred that the two radiation sources 21 and 22 face each other and that at least one contact lens package 23 which is to be sterilized is placed between the radiation sources, preferably on a quartz plate, not shown. It is further preferred that the radiation sources have reflectors 24 and 25 which reflect the light toward the packages(s) 23, and that the reflectors, radiation sources and packages are completely enclosed in a light-tight housing 26 while the radiation sources pulse, so that, when the system is operated, substantially no light from outside the housing can get into the housing and substantially no light from inside the housing can get out.

The integrating sphere 27 is located within the housing 26. In the preferred embodiment the integrating sphere is located between the two radiation sources 21 and 22. The preferred location of the integrating sphere is substantially between the two radiation sources 21 and 22 adjacent to and more preferably in-line with the package(s) to be exposed. The integrating sphere has two entry ports 28 and 29. The entry ports 28 and 29 are preferably located on the integrating sphere 27 at approximately 45° from the midpoint of the package(s) as indicated in FIG. 2. The integrating sphere 27 transmits the radiation it collects to the spectrometer 31 via a fiber optic 30. FIG. 2 only shows one optical sensor location; however, in the preferred embodiment at least one additional optical sensor is placed around the perimeter of the package.

The fiber optic 30 preferably transfers the radiation from the integrating sphere 27 to the spectrometer 31 through the housing 26. In the preferred embodiment as shown the integrating sphere 27 is located inside the housing 26 and the spectrometer 31 is located outside of the housing 26, although the integrating sphere 27 and the spectrometer 31 can both be located inside the housing.

The location of the spectrometer outside the housing aids in reducing the noise in the spectrometer due to electromagnetic interference (EMI) near the electrical cables, and connectors for the radiation source inside the housing. Alternatively, if EMI shields are provided, the spectrometer could be located inside the housing; however, as discussed earlier it is preferred that the spectrometer be located such that it does not block any of the radiation which would otherwise reach the product. The placement of the spectrometer a distance away from the sterilization chamber has the additional benefit of significantly lowering thermal drift in the measurements since only a portion of the sterilization energy will reach the sensor in the spectrometer. By locating the housing of the spectrometer away from the interior of the sterilization chamber, the ambient temperature of the spectrometer is maintained at a more constant temperature without the use of additional thermal cooling or insulation.

The invention is further described in reference to the following examples.

EXAMPLE 1

Figure 3:
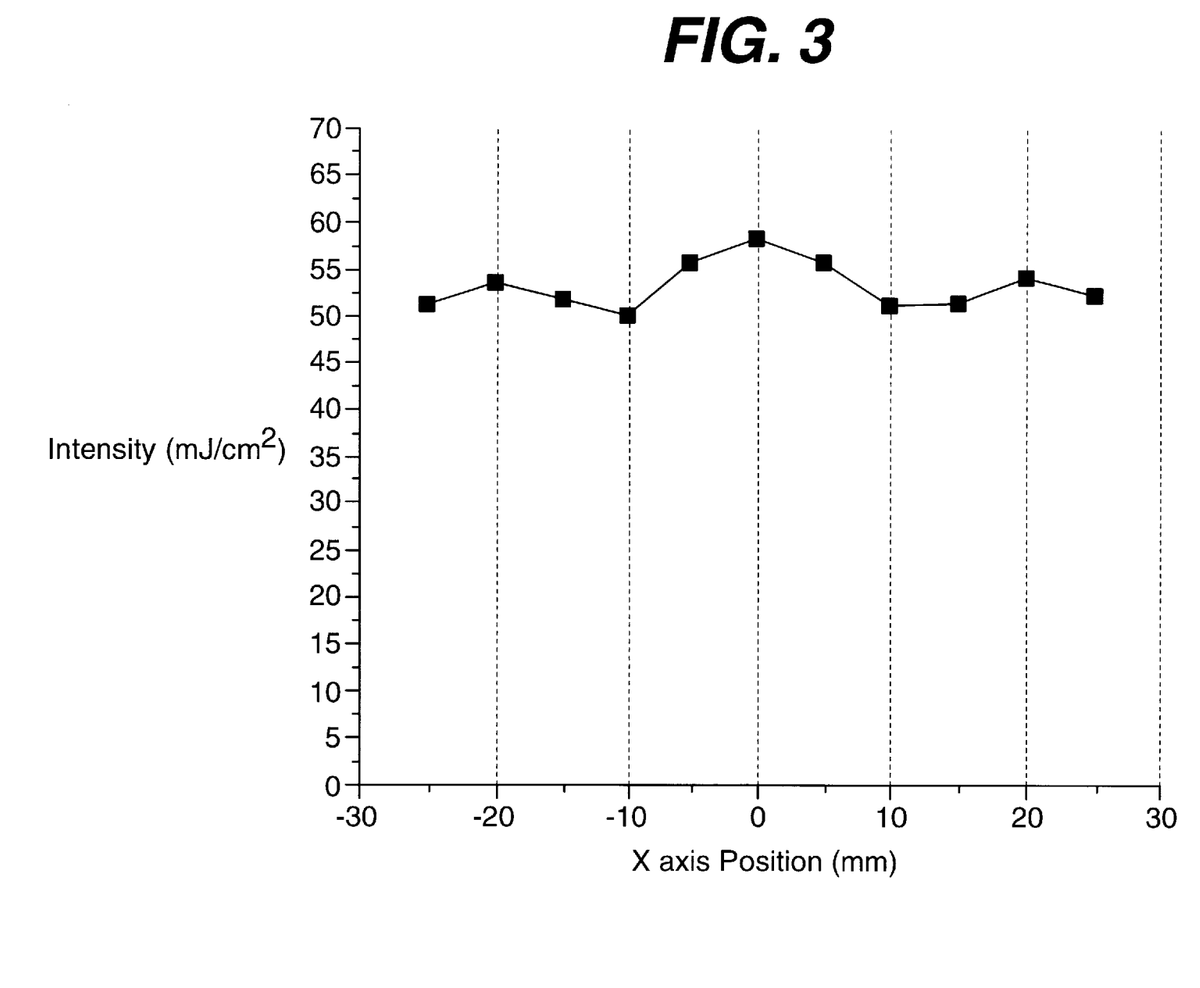
FIG. 3 shows a spectroradiometric map of a single radiation source.

The control system described herein was used to generate a spectroradiometric map of a single radiation source for a PurePulse PB1-4 system. The radiation between from 240 to 280 nm was measured at 21 mm from one of two lamps, at a power level of 52%. The radiation was measured in 5 mm increments −25 mm to 25 mm from the center of lamp perpendicular to the axis of the lamp. The graph produced by the system is shown in FIG. 3.

EXAMPLE 2

Figure 4:
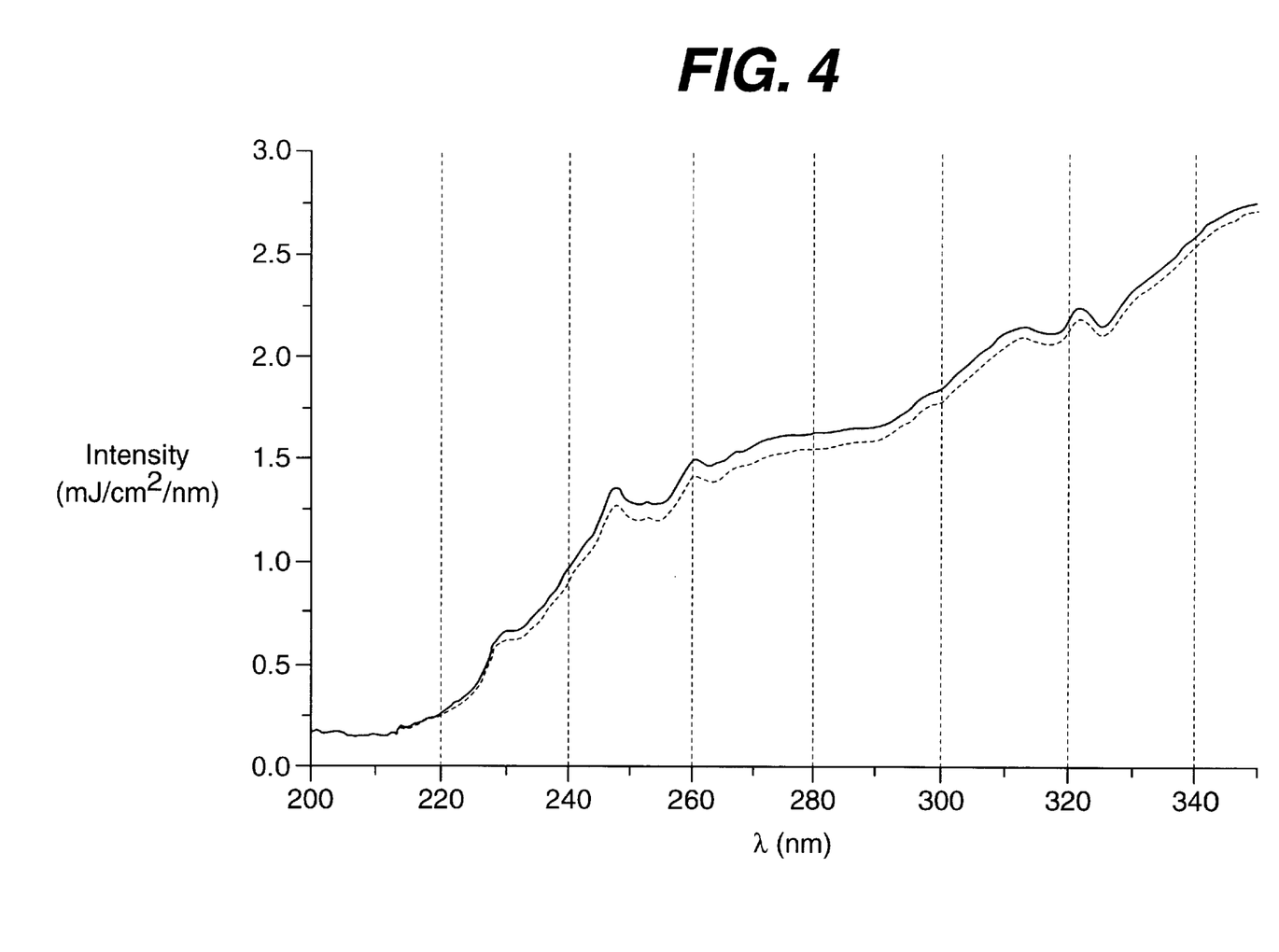
FIG. 4 shows spectroradiometric measurements of a lamp when the lamp was new and the same lamp after 2600 flashes.

Spectroradiometric measurements of a lamp were made when the lamp was new and after 2600 flashes of the lamp. Although the total energy of the lamp had only decreased by 3.4% (as measured with a thermopile calorimeter), FIG. 4 shows that the energy of the lamp between 240 and 280 nm (the range of radiation critical for sterilization) had decreased by 8.6%. The change in the energy of the lamp between 240 and 280 nm, was enough to result in the survival of the more resistant microorganisms; however, this change would not be detected by a system which only measures the change in the overall energy. In FIG. 4, the spectroradiometric measurements of the new lamp are the solid line, and the spectroradiometric measurements of the lamp after 2600 flashes is the dashed line.

This invention has been described with reference to particular embodiments; however, additional embodiments which fall within the scope of the claims will be apparent to those of ordinary skill in the art.

We claim:

1. A sterilization system for a product comprising: radiation source, optical sensor, and timing means, wherein the measurement of energy by said sensor is substantially synchronized based on said timing means to the start and end of each pulse of radiation from said radiation source or to the start and end of the exposure of a product to said radiation source, said sterilization system further comprising a computer, wherein said computer monitors said measurement of energy to determine if said product receives a sterilizing dose of radiation, and further wherein said optical sensor can measure the spectroradiometric flux of individual pulses of radiation which are delivered with less than 5 seconds between the pulses.

2. The sterilization system of claim 1, wherein said optical sensor is a photon-counting sensor.

3. The sterilization system of claim 1, wherein said computer interfaces with said radiation source, said sensor, and said timing means.

4. The sterilization system of claim 1 further wherein just prior to said measurement of said radiation said optical sensor measures the background radiation.

5. The sterilization system of claim 1, wherein said optical sensor comprises an integrating sphere.

6. The sterilization system of claim 1, wherein said optical sensor comprises a cosine receptor.

7. The sterilization system of claim 1, wherein said optical sensor comprises a cosine receptor, an ultraviolet transmitting light guide, and a spectroradiometer.

8. The sterilization system of claim 1, wherein said sterilization system further comprises a housing for said radiation source, said housing being light-tight when said radiation source produces radiation.

9. The sterilization system of claim 1, wherein said sterilization system comprises at least two radiation sources.

10. The sterilization system of claim 9, wherein said sterilization system comprises at least two flashlamps.

11. The sterilization system of claim 10, wherein said flash lamps pulse substantially simultaneously.

12. The sterilization system of claim 1, wherein said optical sensor can measure the spectroradiometric flux of individual pulses of radiation which are delivered with less than 300 milliseconds between the pulses.

13. The sterilization system of claim 1, wherein said optical sensor comprises a spectroradiometer comprising a dispersive optical element, and a photodiode array.

14. The sterilization system of claim 13, wherein said dispersive optical element comprises a holographic grating.

15. The sterilization system of claim 1, further comprising a computer which comprises one or more algorithms which relate the measured radiation to an acceptable range of radiation required for sterilization.

16. The sterilization system of claim 15, wherein said computer further comprises one or more algorithms to control the duration, intensity, frequency, and number of radiation pulses.

17. The sterilization system of claim 1, wherein said system comprises more than one optical sensor.

18. The sterilization system of claim 1, wherein said system further comprises an electrical sensor which measures the voltage or current of said radiation source.

19. The sterilization system of claim 18, further comprising a computer, said computer comprises at least one algorithm which relates the measured voltage or current to an acceptable range of voltage or current required for sterilization.

20. The sterilization system of claim 1, further comprising more than one electrical sensor, one of which measures voltage, another of which measures current.

21. The sterilization system of claim 1, further comprising an electrical sensor which measures the voltage or current of said radiation source.

22. A method of measuring the energy of a radiation source in a sterilization system, wherein said sterilization system comprises said radiation source, an optical sensor, and a timing means, comprising the steps of: dumping the dark current from said optical sensor, substantially synchronizing based on said timing means the measurement of energy by said sensor to the start and end of each pulse of radiation from said radiation source or to the start and end of the exposure of a product to said radiation, and determining if said measured energy is within an acceptable range of energy required for sterilization.

23. The method of claim 22, wherein said sterilization system further comprises an electrical sensor, and the steps of substantially synchronizing based on said timing means the measurement of voltage or current of said radiation source by said electrical sensor to the start and end of each pulse of radiation from said radiation source or to the start and end of the exposure of a product to said radiation, and determining if said measured energy is within an acceptable range of energy required for sterilization.

24. The method of claim 23, further comprising after said substantially synchronizing step during which the voltage or current of said radiation source is measured, the step of: determining if said measured voltage or current from said substantially synchronizing step is sufficient for sterilization.

25. The method of claim 22, wherein before said synchronizing step said method further comprises the steps of: instructing said radiation source to discharge radiation, and measuring time by said timing means from said instructing step.

26. The method of claim 25, wherein after said measuring step, and to accomplish said substantially synchronizing step, said method further comprises the steps of: activating and deactivating said sensor by said timing means after said timing means measures set amounts of time.

27. The method of claim 22, wherein said timing means comprises an electrical, optical or mechanical switch, or combinations of these switches.

28. The method of claim 27, wherein said timing means is a solid state electronic timer.

29. The method of claim 22, wherein prior to said synchronizing step, and after said dumping step, said method further comprises the steps of: spectroradiometrically measuring the background radiation for the same time interval said optical sensor will measure the radiation from said radiation source, and after said synchronization step during which said radiation of said radiation source is measured spectroradio-metrically, said method further comprises the step of: subtracting the spectral amounts of said background radiation from the spectral radiation measured.

30. The method of claim 29, wherein prior to said dumping step, and before said synchronizing step, said method further comprises the step of: instructing said radiation source to discharge radiation; and responding by said radiation source that said radiation source will discharge radiation, which causes said timing means to start measuring time, and further wherein said method is used to sterilize a contact lens in a package.

31. The method of claim 30, wherein said radiation source is a pulsed radiation source.

32. The method of claim 29, wherein after said subtracting step, said method further comprises the step of determining if the measured radiation is within an acceptable range of radiation required for sterilization.

33. The method of claim 22, wherein prior to said substantially synchronizing step, said method further comprises the step of: measuring the radiation at various locations in the volume to receive product to be sterilized by said method to establish a spatial distribution of said radiation from said radiation source.

34. A method of claim 33, wherein said product comprises a package and wherein said method further comprises the step of determining the transmissivity of said package to said radiation.

35. The method of claim 33, wherein after said synchronizing step during which said radiation of said radiation source is measured spectroradiometrically, said method further comprises the step of using said spatial distribution to determine if said package received a sterilizing dose of said radiation.

36. The method of claim 22, wherein said system comprises more than one optical sensor.

37. A sterilization system for a product comprising: radiation source, optical sensor, and timing means, wherein the measurement of energy by said sensor is substantially synchronized based on said timing means to the start and end of each pulse of radiation from said radiation source or to the start and end of the exposure of a product to said radiation source, said sterilization system further comprising a computer, wherein said computer monitors said measurement of energy to determine if said product receives a sterilizing dose of radiation, and further wherein less than 200 milliseconds prior to said measurement of energy by said optical sensor, the dark current is dumped from said optical sensor.

38. The sterilization system of claim 37, wherein said optical sensor comprises a spectrometer.

39. The sterilization system of claim 37, wherein said optical sensor comprises a spectroradiometer.

40. The sterilization system of claim 39, further comprising an electrical sensor which measures the voltage or current of said radiation source.

41. The sterilization system of claim 37, wherein said optical sensor comprises an integrating sphere, and a spectroradiometer.

42. The sterilization system of claim 41, wherein said optical sensor comprises an ultraviolet transmitting light guide.

43. A sterilization system for a product comprising: radiation source, optical sensor, and timing means, wherein the measurement of energy by said sensor is substantially synchronized based on said timing means to the start and end of each pulse of radiation from said radiation source or to the start and end of the exposure of a product to said radiation source, said sterilization system further comprising a computer, wherein said computer monitors said measurement of energy to determine if said product receives a sterilizing dose of radiation, said sterilization system further comprising: a housing; and wherein said optical sensor comprises a means for collecting a portion of said radiation from said radiation source and a spectroradiometer, said means for collecting being located inside said housing, said spectroradiometer being located outside said housing, and said housing being light-tight when said radiation source produces radiation, wherein said spectroradiometer receives radiation input from said means via a fiber optic, said spectroradiometer comprises a photodiode array and a dispersive optical element.

44. The sterilization system of claim 43, wherein said means for collecting is an integrating sphere.

45. The sterilization system of claim 43, wherein said means for collecting is a cosine receptor.

46. The sterilization system of claim 43, wherein said system is used to sterilize packages containing contact lenses.

47. The sterilization system of claim 43, further comprising an additional sensor which detects any stray or extra flashes.

* * * * *